(12) United States Patent
Thornton

(10) Patent No.: US 6,549,802 B2
(45) Date of Patent: Apr. 15, 2003

(54) SEED LOCALIZATION SYSTEM AND METHOD IN ULTRASOUND BY FLUOROSCOPY AND ULTRASOUND FUSION

(75) Inventor: Kenneth B Thornton, Charlottesville, VA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 09/875,031

(22) Filed: Jun. 7, 2001

(65) Prior Publication Data

US 2002/0193677 A1 Dec. 19, 2002

(51) Int. Cl.⁷ .............................. A61B 6/00; A61B 8/00
(52) U.S. Cl. ......................................... 600/426; 60/439
(58) Field of Search ................................ 600/407, 409, 600/426, 437, 439, 427; 382/131

(56) References Cited

U.S. PATENT DOCUMENTS

| | | | | |
|---|---|---|---|---|
| 5,099,846 A | * | 3/1992 | Hardy | 606/130 |
| 5,447,154 A | * | 9/1995 | Cinquin et al. | 600/437 |
| 5,531,227 A | * | 7/1996 | Schneider | 600/407 |
| 5,737,506 A | * | 4/1998 | McKenna et al. | 395/125 |
| 6,006,126 A | * | 12/1999 | Cosman | 600/426 |
| 6,049,729 A | * | 4/2000 | Cook et al. | 600/407 |
| 6,083,167 A | * | 7/2000 | Fox et al. | 600/439 |
| 6,148,095 A | * | 11/2000 | Prause et al. | 382/131 |
| 6,167,296 A | * | 12/2000 | Shahidi | 600/427 |
| 6,206,832 B1 | * | 3/2001 | Downey et al. | 600/439 |
| 6,222,544 B1 | * | 4/2001 | Tarr et al. | 345/349 |
| 6,256,529 B1 | * | 7/2001 | Holupka et al. | 600/427 |
| 6,311,084 B1 | * | 10/2001 | Cormack et al. | 600/411 |
| 6,327,490 B1 | * | 12/2001 | Spetz | 600/427 |

OTHER PUBLICATIONS

Haworth, Annette, et al., "Registration of Prostate Volume With Radiographically Identified Iodine–125 Seeds for Permanent Implant Evaluation," 16 Journal of Brachytherapy International, No. 3, Jul.–Sep. 2000, pp. 157–167.

* cited by examiner

Primary Examiner—Francis J. Jaworski
(74) Attorney, Agent, or Firm—Bingham McCutchen LLP

(57) ABSTRACT

A seed localization system and method in which a computer-based system is used to determine the three-dimensional (3D) position of radiotherapy seeds with respect to an area of affected tissue, such as the prostate, using ultrasound (US) and fluoroscopy (FL) imaging, so that a radiotherapy dose may be calculated. One embodiment the present invention may be used to determine the 3D position of implanted brachytherapy seeds. An alternative embodiment of the invention may be used to determine the 3D position of implanted objects other than brachytherapy seeds. The seed localization system and method includes a graphical user interface useful for assisting a user of the seed localization system in its operation.

60 Claims, 9 Drawing Sheets

SEED LOCALIZATION SYSTEM AND METHOD IN ULTRASOUND BY FLUOROSCOPY AND ULTRASOUND FUSION

BACKGROUND OF THE INVENTION

1. Field of the Invention

This invention relates generally to systems and methods for the treatment of cancer using radiation, and, more specifically, to systems and methods for the treatment of cancer using implanted brachytherapy seeds.

2. Background

Brachytherapy, a useful technique for treating cancer, is a radiation treatment using a solid or enclosed radioisotopic source on the surface of the body or a short distance from the area to be treated. With respect to prostate cancer, for example, brachytherapy involves the implantation of radiotherapy seeds into the prostate. The effectiveness of the brachytherapy treatment depends, however, on the particularized placement of the implanted brachytherapy seeds to achieve a preferred radiotherapy dose.

The radiotherapy dose administered to the patient may be calculated by observing the three dimensional (3D) positions of the brachytherapy seeds with respect to the affected tissue. Computed tomography (CT) is one technique used to determine the three dimensional locations of the seeds. A common problem with using CT, however, is that many operating rooms do not contain CT equipment. This makes it impossible to evaluate and subsequently adjust the dose of radiotherapy while the patient is in the treatment position. For example, if "cold spots" are found after imaging with CT, then the patient must be retreated.

Therefore, it would be advantageous to provide a system and method that provide the capability of determining the three-dimensional location of brachytherapy seeds without requiring use of CT.

Patent

Figure 2:
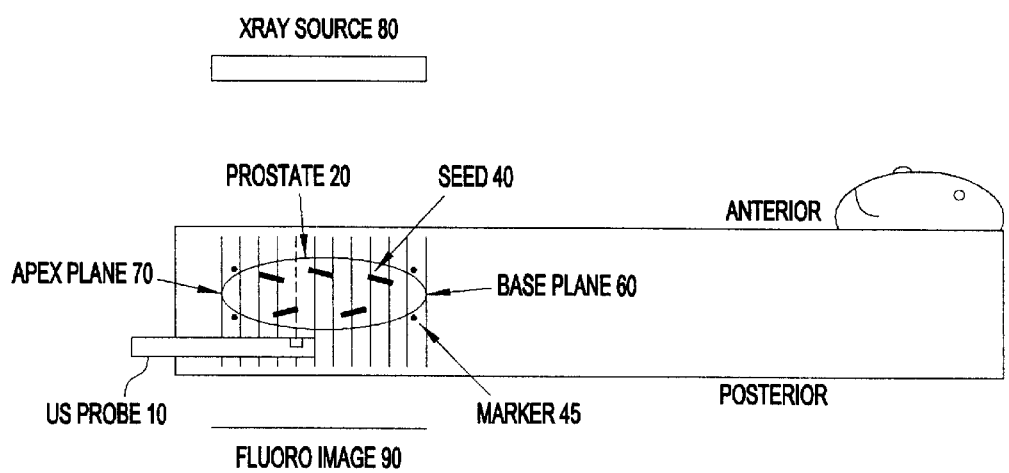
FIG. 2 is a side view of an implant geometry used with an embodiment of the present invention.
Figure 2A:
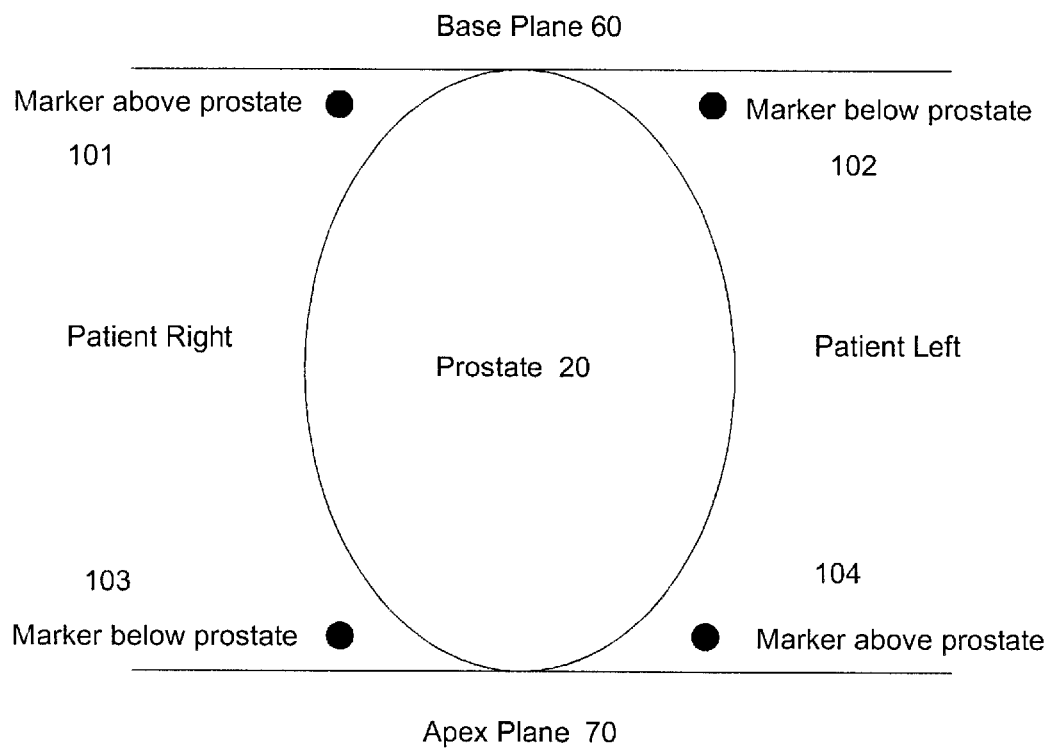
FIG. 2a is an anterior-posterior (AP) view of an implant geometry showing the positions of the implanted markers used with an embodiment of the present invention.
Figure 2B:
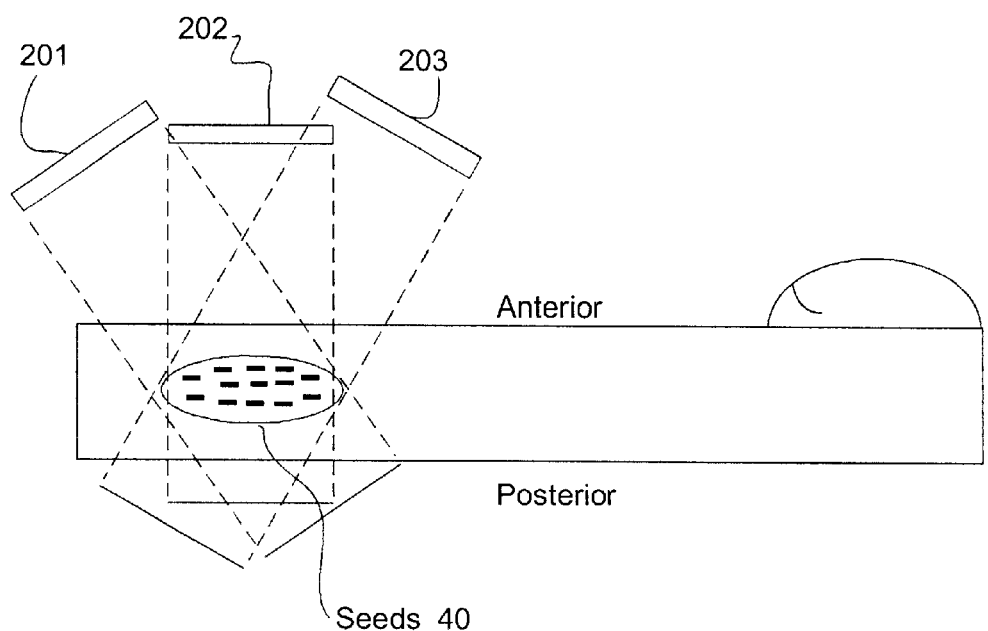
FIG. 2b is a side view illustrating the geometry of FL image capture used in an embodiment of the present invention.
Figure 2C:
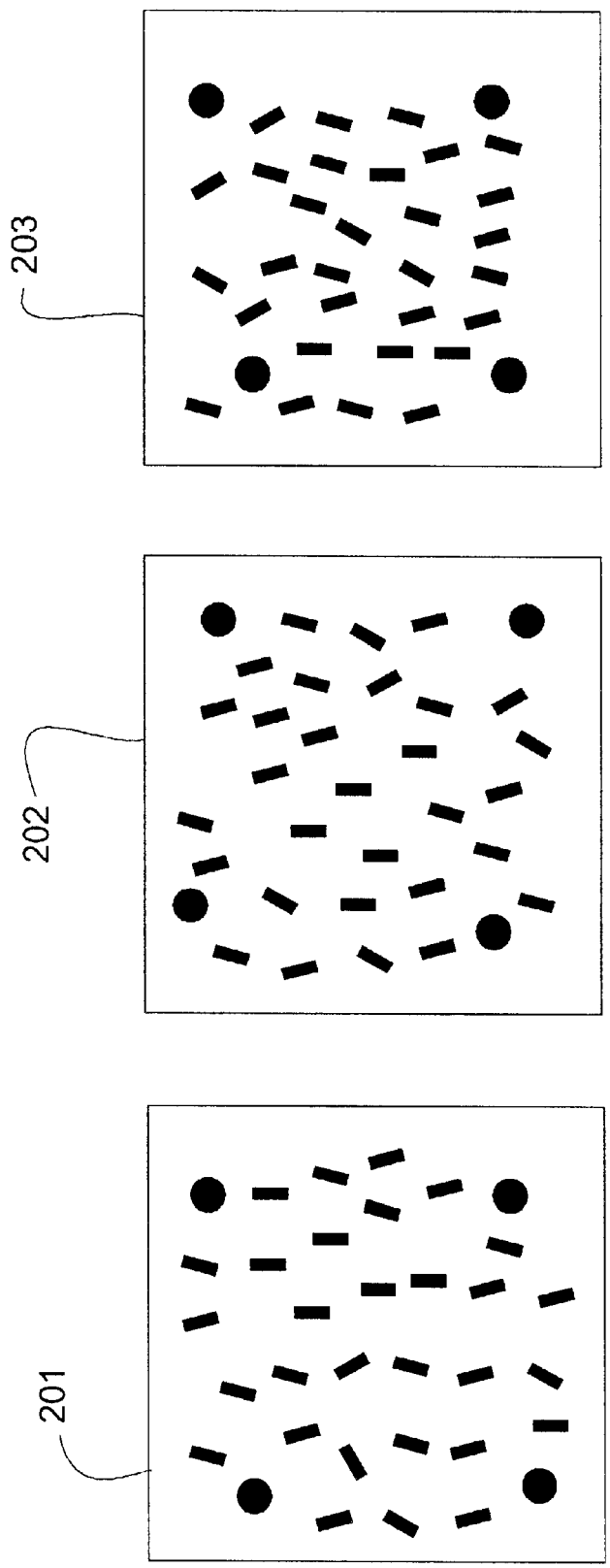
Figure 3:
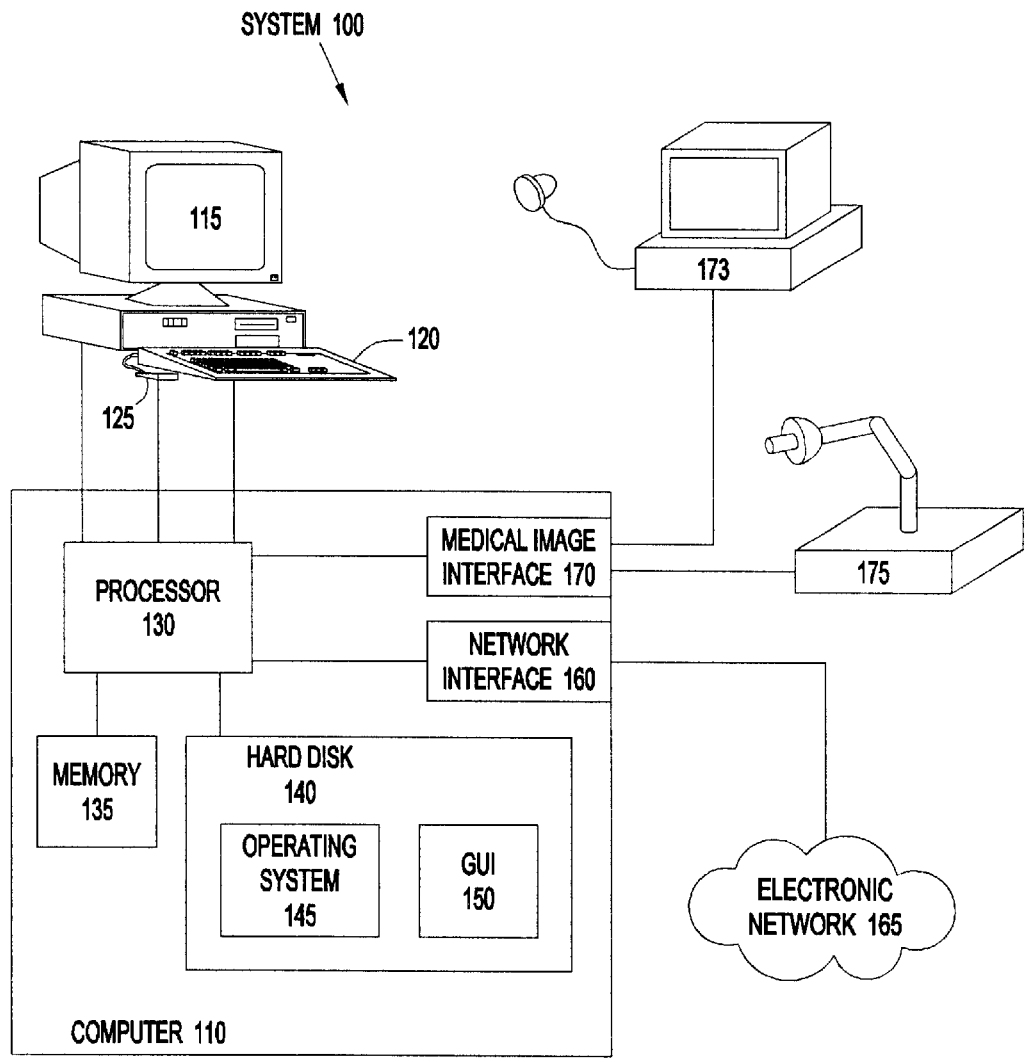
Figure 4:
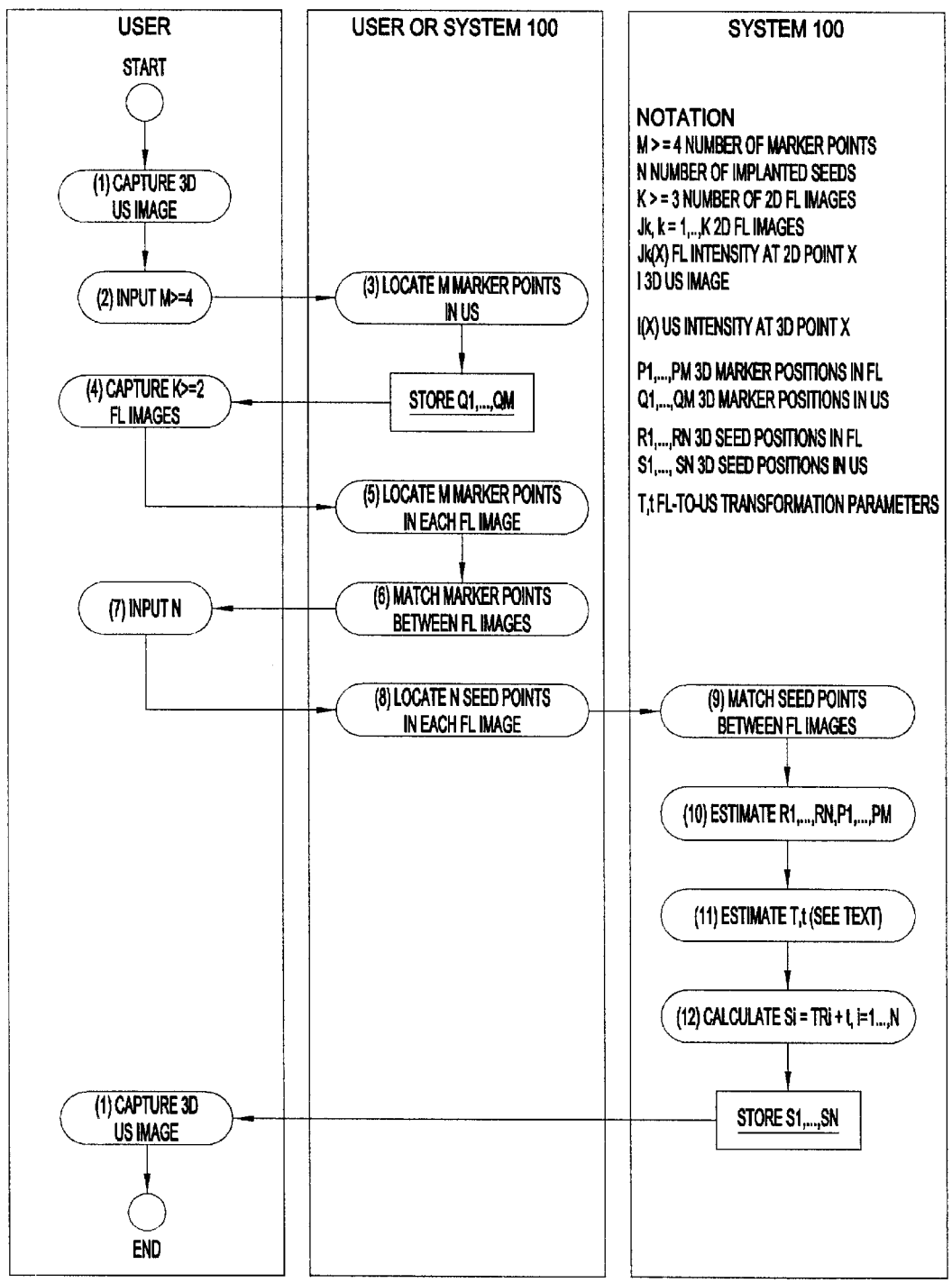
Figure 5:
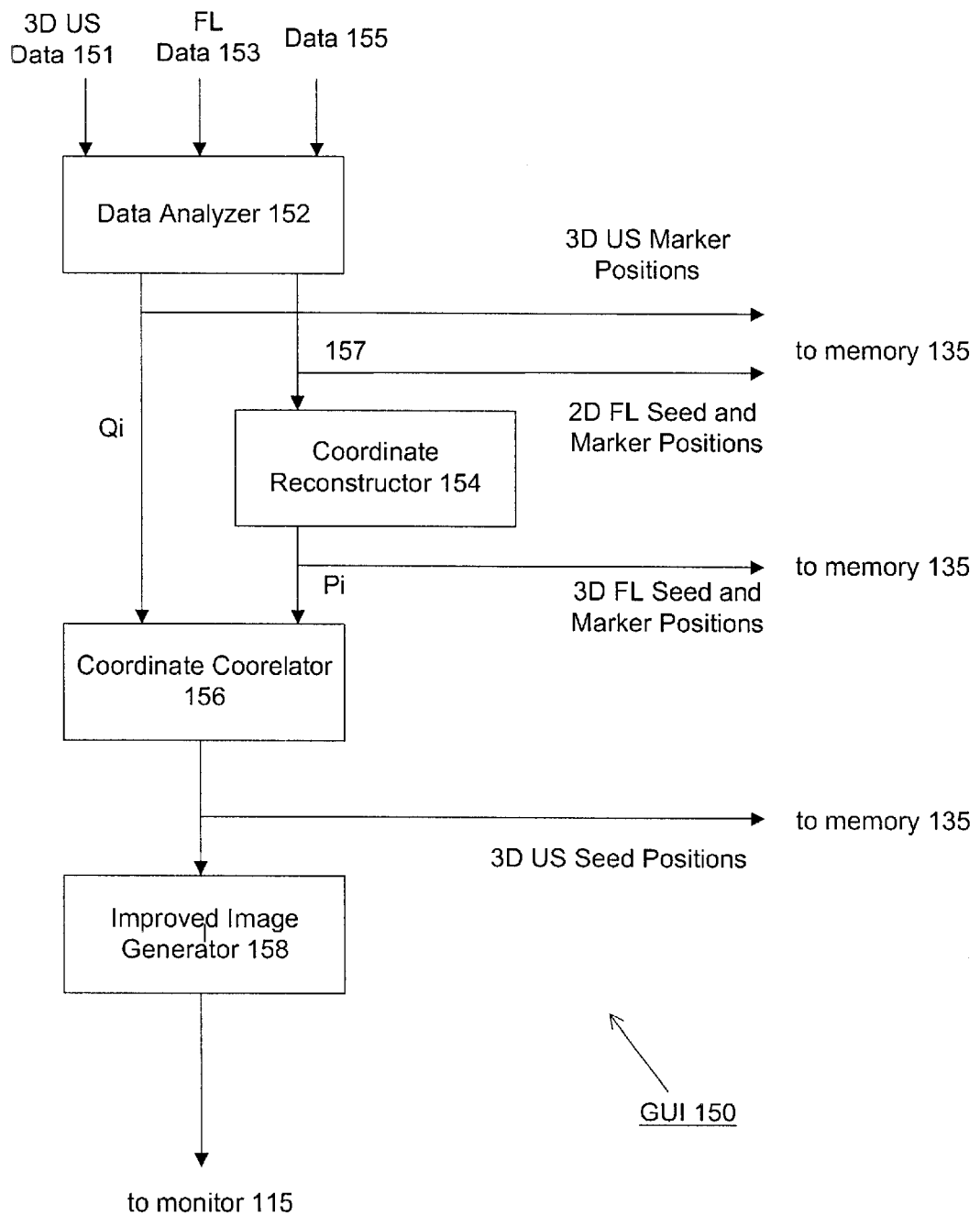
Figure 6:
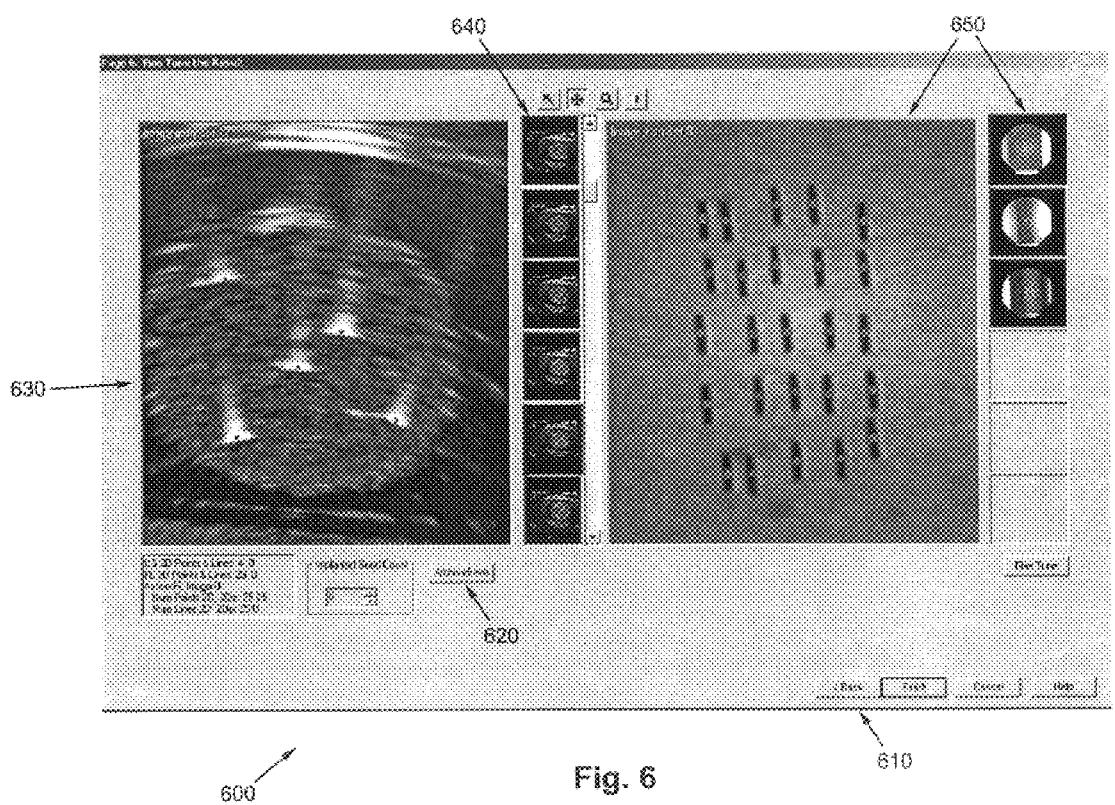

FIG. 2c is a schematic illustration of three FL images showing markers distinguishable from seeds;

FIG. 3 is a block diagram of an embodiment of the system of the present invention;

FIG. 4 is a flow chart diagram of an embodiment of a method according to the present invention;

FIG. 5 is a block diagram of the structure of a graphical user interface of an embodiment of the present invention; and FIG. 6 is a screen shot display of the graphical user interface according to an embodiment of the present invention.

SUMMARY OF THE INVENTION

The present invention provides a system and method for determining the three-dimensional (3D) position of implanted radiotherapy seeds with respect to an area of affected tissue, such as the prostate, so that a radiotherapy dose may be calculated. While in one aspect the invention determines the 3D position of implanted brachytherapy seeds, in another aspect the invention determines the 3D position of implanted objects other than brachytherapy seeds (e.g. fiducial markers). The present invention uses ultrasound (US) a nd fluoroscopy (FL) imaging and does not require computed tomography (CT) imaging.

In one aspect, the invention provides a method and system for determining the position of implanted seeds with increased accuracy by determining the 3D seed positions in the most recently acquired US treatment volume/image, or group of US treatment data.

The present invention also provides a system and method for determining the 3D position of implanted radiotherapy seeds with respect to an area of affected tissue such that the dosimetry to the affected tissue may be determined intraoperatively, permitting dynamic adjustment of the treatment plan.

The present invention further provides a system and method of user visualization of the 3D position of implanted brachytherapy seeds by providing an interactive, computer-generated, graphical user interface.

Those of skill in the art, upon inspection of this specification and the drawings hereto, will appreciate that many features and variations are provided by the system and method according to the present invention.

DETAILED DESCRIPTION OF THE INVENTION

The present invention comprises a system and method for determining the three-dimensional (3D) position of radiotherapy seeds with respect to an area of affected tissue, such as the prostate, using ultrasound (US) and fluoroscopy (FL) imaging, so that a radiotherapy dose may be calculated. One embodiment of the present invention may be used to determine the 3D position of implanted brachytherapy seeds. An alternative embodiment of the invention may be used to determine the 3D position of implanted objects other than brachytherapy seeds.

Figure 1:
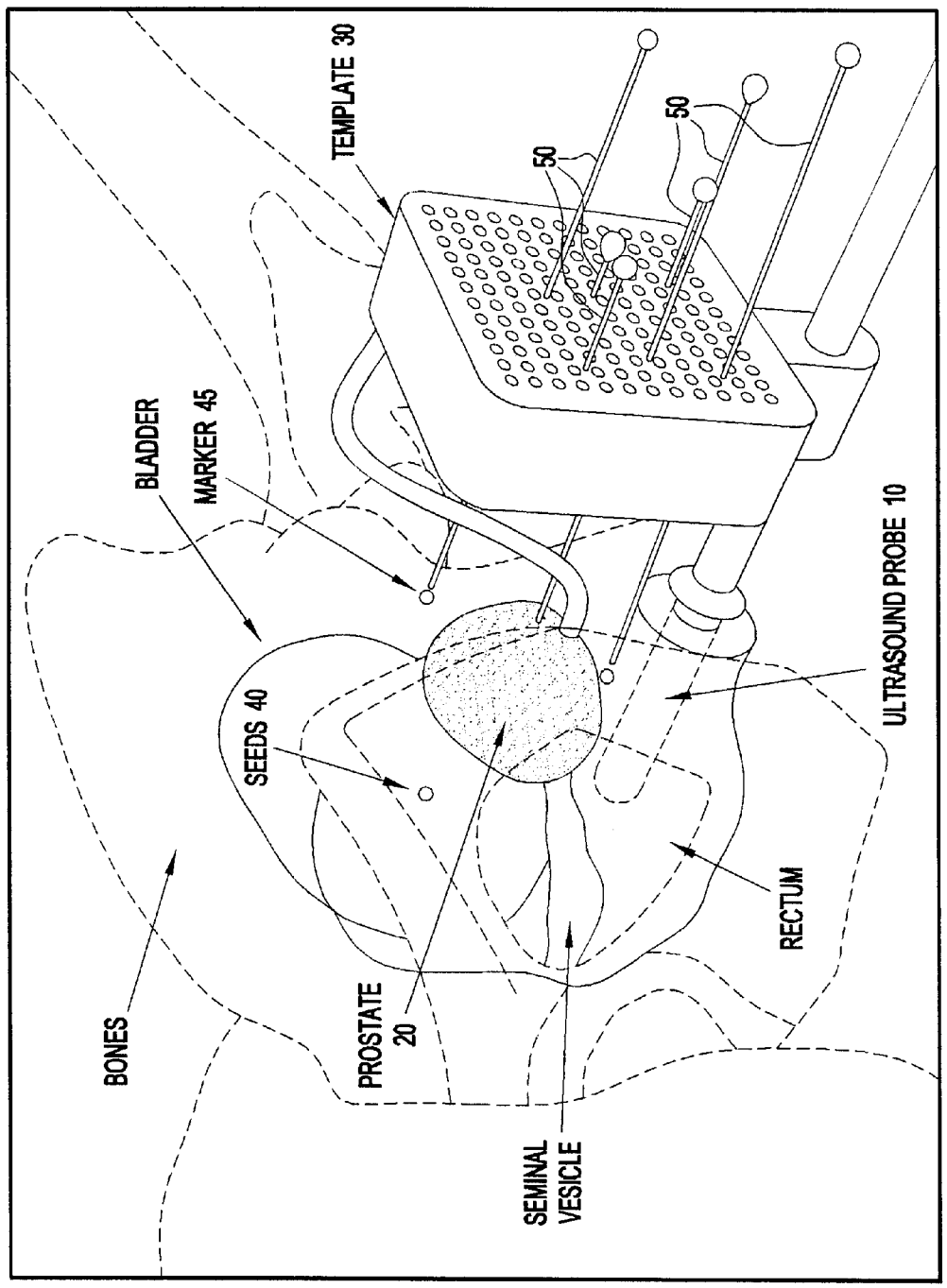
FIG. 1 is a three dimensional illustration of a preferred implant geometry used to orient the coordinate space for the system and method of the present invention.

FIG. 1 illustrates a 3D view of the implant geometry of one embodiment of the invention. Referring now to FIG. 1, an ultrasound probe 10 is inserted into the rectum (beneath prostate 20) and images are formed in vertical slices through prostate 20. These vertical image slices are planes parallel to the plane of template 30 and orthogonal to the axis of probe 10. The "base" and "apex" planes of the prostate (not shown) are the vertical planes farthest from the template 30 and closest to template 30, respectively. Typically in standard practice, a therapist plans where within a region of prostate 20 to implant brachytherapy seeds 40. Brachytherapy seeds 40 are typically cylinders 0.8 mm in diameter and 4.5 mm in length. The planned 3D position of a seed 40 is specified by a triple of (x,y,z) coordinates specifying the center of the seed 40 cylinder. The (x,y) coordinates of the triple correspond to one of the holes in template 30. The x coordinate corresponds to the horizontal axis of template 30 and the y coordinate corresponds to the vertical axis of template 30. The z coordinate is the depth within prostate 20 (i.e. some vertical plane parallel to template 30, between the apex and the base, and orthogonal to the axes of probe 10 and needles 50). Markers 45 are preferably spherical in shape to distinguish them from seeds 40, although other shapes are possible. Markers 45 are inserted prior to inserting seeds 40 and may be placed around the periphery of the prostate 20. Markers 45 are not coplanar. (By definition, A set of N points $\{(x_i,y_i,z_i) i=1, \ldots, N\}$ are coplanar if and only if there exists 4 constants A,B,C,D such that $A^2+B^2+C^2 \neq D^2 \neq 0$ and $Ax_i+By_i+Cz_i+D=0$ for all i=1, ..., N.)

Further details concerning radioactive seed implant planning, delivery, and verification may be found in Walliner, Kent et al., "Prostate Brachytherapy Made Complicated," SmartMedicine Press, Seattle, Wash. 1997, the entire disclosure of which is hereby incorporated into this specification as if set forth herein. Further details concerning standards for practice with respect to prostate seed implant brachytherapy may be found in articles by Yu, Yan et al., "Permanent Prostate Seed Implant Brachytherapy: Report of the American Association of Physicists in Medicine Task Group No. 64," Medical Physics, Volume 26, No. 10, October 1999, pp. 2054–2076, and Nag, Subir et al., "American Brachytherapy Society (ABS) Recommendations for Transperineal Permanent Brachytherapy of Prostate Cancer," International Journal of Radiation Oncology Biology Physics," Volume 44, No. 4, 1999, pp. 789–799, the entire disclosures of which are hereby incorporated into this specification as if set forth herein.

As shown in FIG. 1, template 30 is registered with respect to ultrasound probe 10. Brachytherapy seeds 40 may be preloaded into hollow needles 50 (though other methods are possible) and placed through specific pre-planned holes in template 30. Needles 50 are inserted into prostate 20 using template 30 as a guide until they are seen on the ultrasound image appearing on an ultrasound image monitor (not shown). The therapist may then appropriately position seeds 40 within prostate 20. Seeds 40 are held in place by a central stylet while needles 50 are withdrawn, leaving seeds 40 embedded at discrete locations within a region of prostate 20.

In an alternative embodiment, seeds 40 in FIG. 1 may represent implanted objects other than brachytherapy seeds. Further, in another alternative embodiment of the invention the tissue to be treated may be tissue other than prostate 20.

FIG. 2 is a side view of one embodiment of the implant geometry. Referring now to FIG. 2, cylindrical seeds 40 are located in prostate 20 at points usually between the base plane 60 and apex plane 70. Markers 45, often spherical, may be placed around the periphery of prostate 20. Prostate 20, typically 40–60 mm in length, is well visualized in the US, but cannot be as clearly seen in the FL 90. Seeds 40 are well visualized in the FL 90, but cannot always be seen in the US. Referring back to FIG. 1, implant needles 50 and markers 45 can be seen in both the US and the FL 90. Only five brachytherapy seeds 40 are shown in FIG. 2, although typically 70–120 seeds are implanted.

In an alternative embodiment of the invention, seeds 40 in FIG. 2 may represent implanted objects other than brachytherapy seeds. Further, in another alternative embodiment of the invention the tissue to be treated may be tissue other than prostate 20.

FIG. 2a illustrates an anterior-posterior (AP) view of the implanted markers 45. In a preferred embodiment, at least four markers 45 are implanted around the periphery of prostate 20. In one embodiment of the present invention, as shown in FIG. 2a, near apex plane 70 the left marker 103 is below prostate 20 and the right marker 104 is above prostate 20. Markers 45 are preferably not located in the same plane as seeds 40. To prevent the markers 45 from being coplanar, the opposite convention is used near base plane 60, i.e., the left marker 101 is above prostate 20 and the right marker 102 is below prostate 20. The markers 45 are preferably chosen for imaging characteristics that allow them to be distinguishable from seeds 40. Since seeds 40 are typically cylindrical, in one embodiment of the invention the markers 45 are spherical.

FIG. 2b illustrates a side view of the FL imaging geometry. At least two FL images of the prostate seeds 40 and markers 45 are necessary. By way of example, three FL images 201, 202, and 203 are shown in FIG. 2b. The therapist can orient the FL imaging equipment "on-line" to maximize the visibility of seeds 40 and markers 45. For example, in some imaging positions, many of the seeds may overlap and not be distinguishable. These positions are to be avoided. As those skilled in the art will appreciate, imaging positions with greater "disparity" (i.e., greater separation between the images) lead to more accurate 3D reconstruction of the seed and marker positions.

FIG. 2c is a schematic illustration of three FL images 201–203. At least two FL images of the seeds 40 and markers 45 are necessary. Markers 45 may be chosen to be easily distinguishable from seeds 40. The seeds 40 and markers 45 in each image are located. The markers 45 are matched between the images as described herein. There are typically 70–120 implanted seeds in the prostate. Once the markers are matched, the seeds 40 can be matched automatically as described herein.

FIG. 3 illustrates seed localization system 100 according to an embodiment of the present invention. In one embodiment, seed localization system 100 is implemented using programmed instructions executing on a standard personal computer platform. In this embodiment seed localization system 100 includes a personal computer 110 having a standard set of peripherals, including a color monitor 115 or other suitable monitor, keyboard 120, mouse 125, microprocessor 130, memory 135, non-volatile storage such as a hard disk drive 140, and a standard operating system software 145 such as Microsoft® Windows™. In one embodiment, system 100 is also connected to an electronic network 165 through a network interface 160. In one embodiment, application software instructions are implemented in seed localization system 100 using the C++ programming language. Seed localization system 100 is capable of storing image data and processing stored image data in the manner described herein. In one embodiment, a user interacts with seed localization system 100 using graphical user interface 150.

FIG. 4 illustrates an embodiment of a method 200 according to the present invention. Each step corresponds to a cell in FIG. 4. By way of example only, each step is numbered. The ordering or combination of the following steps may differ from the numerical ordering in FIG. 4 as would occur to one of ordinary skill in the art. Further, the column labeled "User or System 100" denotes that the steps therein may be performed either by the user (using system 100) or automatically by system 100, in different embodiments as described below.

Referring now to FIG. 4, the method of the present invention comprises the following steps:

(1) In Step 1, the user selects for input one 3D US image of the prostate 20. Any one of several methods or combinations thereof may be used to acquire a 3D US image. In one embodiment, the 3D image is "captured" directly from an ultrasound imaging device 173 using a medical image interface 170 (shown in FIG. 3). In another embodiment, the 3D image is loaded from non-volatile storage 140 or received via electronic network 165 (shown in FIG. 3) according to standard protocols for medical images, such as "Digital Imaging and Communications in Medicine" (DICOM) protocols.

Any one of several methods or combinations thereof may be used to directly "capture" a 3D US image of prostate 20. In one embodiment, a method is used wherein US probe 10 is moved ("stepped") from base plane 60 to apex plane 70 in small increments, and system 100 acquires a discrete 2D image after each step using the medical image interface 170. The spacing between adjacent images (the step size or Z resolution) is a known value usually less than or equal to 2 mm. The X and Y resolutions of the images are also fixed through a "template registration" process that is known to those skilled in the art. The collection of 2D images are then assembled into a 3D image using standard techniques known to those skilled in the art.

Further details concerning template registration may be found in Mutic, Sasa et al., "A Simple Technique for Alignment of Perineal Needle Template to Ultrasound Image Grid for Permanent Prostate Implants," Medical Physics, Volume 27, No. 1, January 2000, pp. 141–143, the entire disclosure of which is hereby incorporated into this specification as if set forth herein.

(2) In Step 2, the user inputs the number $M \geq 4$ of markers 45 implanted into the prostate. Typically $4 \leq M \leq 8$. If the user does not enter at least $M \geq 4$ an error message is displayed to the user. In an alternative embodiment of the invention, seed localization system 100 retrieves the number of implanted markers 45 from memory 135 or hard disk 140 or another input or memory device. In one embodiment of the invention system 100 receives the number of implanted markers via an electronic network 165 such as via FTP over the Internet (by way of example only).

(3) In Step 3, the user locates the M highly visible markers 45 in the 3D US image using seed localization system 100. M is known from step 2. In an alternative embodiment of the invention, seed localization system 100 may automatically locate M visible markers 45 using a variety of discrimination techniques known to those skilled in the art of medical imaging. The coordinates of these highly visible markers 45 are stored in memory as a series of 3D vectors $Q_1, Q_2, \ldots, Q_M$. By way of example only, the memory in which coordinate vectors are stored may be memory typically associated with the personal computer of system 100 such as memory areas 135 (FIG. 3).

An arbitrary 3D point, X, in the 3D US image has a scalar intensity I(X). Typically, I(X)=0 if the point is completely dark, and I(X)=255 if the point is completely bright. Because seeds 40 and markers 45 reflect more sonic energy than tissue, the seeds and markers appear in the 3D US image with greater scalar intensity, i.e., the seeds and markers show up as bright spots in the 3D US volume (i.e., 3D US image).

(4) In Step 4, the user selects for input K 2D FL images $J_k$, k=1, . . . , K of the prostate 20. In one embodiment of the invention, these images are "captured" directly from a fluoroscopy imaging device 175 using a medical image interface 170. In another embodiment, the 2D images are loaded from non-volatile storage 140 or received via electronic network 165 according to standard protocols for medical images, such as "Digital Imaging and Communications in Medicine" (DICOM) protocols.

Any one of several methods or combinations thereof may be used to directly "capture" a 2D FL image of prostate 20. In one embodiment, a C-arm device consisting of an X-ray source 80 and fluoroscopy image 90 (shown in FIG. 2) is used. The C-arm is positioned at K discrete positions that cut across prostate 20 and such that seeds 40 and markers 45 are visible in the fluoroscopy image 90. At each position, a FL image $J_k$ is acquired using medical image interface 170. The C-arm positions at which the images are acquired do not need to be known and are chosen to maximize the visibility of seeds 40 and markers 45 and to provide "maximum disparity" for reconstruction according to standard techniques known to those skilled in the art. In one embodiment of the invention, US probe 10 is not within the body for enhanced image clarity.

(5) In Step 5, the user locates the M highly visible markers 45 in each 2D FL image $J_k$, k=1, . . . , K using seed localization system 100. M is known from step 2. In an alternative embodiment of the invention, seed localization system 100 may automatically locate M visible markers 45 using a variety of discrimination techniques known to those skilled in the art of medical imaging. Because there are K FL images and M markers, the number of 2D positions determined by system 100 is K×M. In one embodiment of the invention each 2D position is stored in memory 135 for later recall and processing.

An arbitrary 2D point, X, in a 2D FL image $J_k$ has a scalar intensity $J_k(X)$. Typically, $J_k(X)=0$ if the point is completely dark, and $J_k(X)=255$ if the point is completely bright. Because markers 45 absorb more x-ray energy than tissue, the markers appear in the 2D FL image with lesser scalar intensity, i.e., the markers show up as dark spots in the 2D FL image. Recall that the markers 45 may be chosen so that they are distinguishable from the cylindrical seeds 40 in each FL image. In one embodiment of the invention the markers 45 are spherical balls.

(6) In Step 6, in a preferred embodiment the user matches the marker points between the K images, i.e., orders the marker points so that marker point m ($1 \leq m \leq M$) in FL image 1 corresponds to marker point m in FL image 2, and so on through FL image K. In an alternative embodiment, seed localization system 100 may automatically perform these functions according to standard techniques known to those skilled in the art.

(7) In Step 7, the user inputs the number N of brachytherapy seeds 40 implanted using seed localization system 100. Typically 70<N<120. In one embodiment, system 100 requires that the user enter at least $N \geq 1$ seeds 40. If the user does not enter at least $N \geq 1$ an error message is displayed to the user. In an alternative embodiment of the invention, seed localization system 100 retrieves the number of implanted seeds 40 from memory 135 or hard disk 140 or another input or memory device. In one embodiment of the invention system 100 receives the number of implanted seeds via an electronic network 165 such as via FTP over the Internet (by way of example only).

(8) In Step 8, the user locates the N seeds 40 in each 2D FL image $J_k$, k=1, . . . , K using seed localization system 100. N is known from step 7. In an alternative embodiment of the invention, seed localization system 100 may automatically locate the N seeds 40 using a variety of discrimination techniques known to those skilled in the art of medical imaging. Because there are K FL images and N seeds, the number of 2D positions determined by system 100 is K×N. In one embodiment of the invention each 2D position is stored in memory 135 for later recall and processing.

Because seeds 40 absorb more x-ray energy than tissue, the seeds appear in the 2D FL image with lesser scalar intensity, i.e., the seeds show up as dark spots in the 2D FL image.

(9) In Step 9, system 100 automatically matches or correlates the seed points between the K images, i.e., orders the seed points so that seed point n ($1 \leq n \leq N$) in FL image 1 corresponds to seed point n in FL image 2, and so on through FL image K.

(10) In Step 10, system 100 reconstructs, in the FL coordinate system, the 3D seed positions $R_1, R_2, \ldots, R_N$ and the 3D marker positions $P_1, P_2, \ldots, P_M$ according to standard techniques known to those skilled in the art.

(11) In Step 11 seed localization system 100 finds a solution 3×3 matrix T and a 3×1 vector t that maps each 3D FL seed point $R_i$ to its corresponding 3D US location $S_i$. In one embodiment of the invention an initial estimate for the pair (T,t) is found by seed localization system 100 by finding the unique solution to the optimization problem $$\min_{T,t} \sum_{i=1}^{M} \|Q_i - TP_i - t\|^2.$$

Given the initial estimate, a final estimate is found by seed localization system 100 by solving the optimization problem $$\max_{T,t} \sum_{i=1}^{N} I(TR_i + t).$$

The maximization problem may or may not have a unique solution. If the maximization problem has no unique solution, a locally optimal solution may be determined. The maximization operation is useful to optimize the transformation pair (T,t) in order to more precisely correlate the 3D US seed positions to the 3D US image.

(12) In Step 12 seed localization system 100 determines or calculates the 3D seed positions $\{S_i = TR_i + t | i=1, \ldots, N\}$ in the US image and displays them in the 3D US image. Seeds 40 may appear within the 3D US image on the monitor as transparent, colored cylinders.

(13) Using seed localization system 100, the user visualizes the positions of seeds 40 with respect to the 3D US image by viewing the image displayed on the monitor 115.

Thus, a system and method has been shown for determining the three-dimensional (3D) position of implanted brachytherapy seeds with respect to an area of affected tissue. The system and method allows the practitioner to calculate a radiotherapy dose by examining images generated using ultrasound (US) and fluoroscopy (FL) imaging but not requiring computed tomography (CT) imaging. The system may incorporate portable C-arm FL systems as well. There is no requirement to use a fixed (pre-determined) FL imaging geometry or to accurately calibrate the FL images (e.g. each FL image may have a different, unknown magnification). There is also no requirement for a fixed external, fiducial system.

Further, because the present invention reconstructs the seed positions from fluoroscopic images rather than from other images, the invention may be practiced in a wider variety of settings than was possible in the prior art. For example, the invention may be practiced in an operating room. There is no need for a radiotherapy simulator couch or other specialized equipment.

Because the invention may be practiced intraoperatively, the invention does not require the patient to be carefully repositioned in another room having specialized medical imaging equipment. Further, the inventive system and method differs from the prior art in that seed positions are not determined based on planned, pre-implant seed coordinates but rather on the actual 3D seed positions at the time of implant in the most recently acquired US treatment volume/image. Thus, the 3D seed locations are identified much more accurately than in prior art systems and the user may validate the result. The dosimetry to the tissue under treatment may be determined intraoperatively, permitting dynamic adjustment of the treatment plan.

As shown in FIG. 3, one embodiment of the present invention comprises a computer-readable media 135 or 140 (by way of example only) on which is embodied a set of programmed instructions that cause one or more processors 130 to perform a sequence of Steps 1–13 (reference FIG. 4). In one embodiment said processors and computer-readable media are comprised within computer 110. In one embodiment of the invention, computer-readable medium 140 is a hard disk. Operating system 145 and graphical user interface (GUI) 150 are stored on hard disk 140 in one embodiment of the invention.

Referring again to FIG. 3, one embodiment of the invention includes a medical image interface 170. In this embodiment computer 110 acquires ultrasound and fluoroscopic images from ultrasound imaging device 173 and fluoroscopic imaging device 175 respectively. In an alternative embodiment of the invention, a network interface 160 is provided in addition to or instead of medical image interface 170. In this alternative embodiment computer 110 acquires ultrasound and fluoroscopic images through either medical image interface 170 or network interface 160. In one embodiment of the invention medical images are obtained through network interface 160 via a connection to an electronic network 165 as shown.

One embodiment of the present invention comprises a computer-generated, graphical user interface (GUI) 150 to guide the user in accomplishing Steps 1–13 described above (reference FIG. 4). GUI 150 is preferably implemented on computer system 110 using monitor 115, keyboard 120, and mouse 125 in the manner known to those of skill in the art. GUI 150 forms an improved 3D image of the region of implanted seeds by analyzing US and FL data. GUI 150 then allows the user to identify the location of each implanted seed in the region by displaying the improved 3D image.

FIG. 5 illustrates one embodiment of graphical user interface 150 in greater detail. Through processor 130 (FIG. 3), GUI 150 interacts with data input sources such as keyboard 120, mouse 125, memory 135, and hard disk 140. GUI 150 also interacts with medical image interface 170 as well as network interface 160 via processor 130.

From any of these data sources, GUI 150 is provided with 3D US data 151 representing an image of a 3D region of implanted seeds according to Step 1 of the present invention (reference FIG. 4). (References to "Steps" discussed herein are made with respect to FIG. 4.) GUI 150 is also provided with FL data 153 representing a plurality of K FL images of the same region according to Step 4 of the present invention.

Data analyzer 152 analyzes 3D US data 151. In one embodiment of the invention, data analyzer 152 also uses data 155 input from sources 120, 125, 135, 140, 160, or 170 (FIG. 3) to analyze 3D US data 151. Data analyzer 152 receives a number M corresponding to the number of implanted markers according to Step 2 of the present invention. This number M is comprised within data 155.

Data analyzer 152 locates the M highly visible markers according to Step 3 of the present invention. As previously noted, in one embodiment of the invention the user provides input 155 to locate M highly visible markers. In an alternative embodiment, data analyzer 152 automatically locates M highly visible markers using a variety of discrimination techniques known to those skilled in the art of medical imaging.

Data analyzer 152 stores the 3D coordinates of these highly visible markers in memory as a series of vectors $Q_1$, $Q_2, \ldots, Q_M$. By way of example only, the memory in which coordinate vectors are stored may be memory typically associated with the personal computer of system 100 such as memory areas 135 or 140 (reference FIG. 3).

Data analyzer 152 also analyzes FL data 153. Data analyzer 152 locates each implanted marker appearing in each FL image $J_1, J_2, \ldots, J_K$ comprised within FL data 153 according to Step 5 of the present invention. As previously noted, in one embodiment of the invention the user provides input 155 to locate each implanted marker appearing in each FL image $J_1, J_2, \ldots, J_K$. In an alternative embodiment, data analyzer 152 automatically locates each marker using a variety of discrimination techniques known to those skilled in the art of medical imaging.

In one embodiment of the invention, data analyzer 152 stores the FL coordinates 157 of each marker in memory. By way of example only, the memory in which FL coordinates 157 are stored may be memory typically associated with the personal computer of system 100 such as memory areas 135 or 140 (FIG. 3).

Similarly to that described above, data analyzer 152 locates each implanted seed appearing in each FL image $J_1$, $J_2, \ldots, J_K$ comprised within FL data 153 according to Step 8 of the present invention. As previously noted, in one embodiment of the invention the user provides input 155 to locate each implanted seed appearing in each FL image $J_1$, $J_2, \ldots, J_K$. In an alternative embodiment, data analyzer 152 automatically locates each seed using a variety of discrimination techniques known to those skilled in the art of medical imaging.

In one embodiment of the invention, data analyzer 152 stores the FL coordinates 157 of each seed in memory. By way of example only, the memory in which FL coordinates 157 are stored may be memory typically associated with the personal computer of system 100 such as memory areas 135 or 140 (FIG. 3).

According to Steps 6 and 9 of the present invention, coordinate reconstructor 154 receives from data analyzer 152 the discrete 2D positions 157 of each seed (and marker) appearing on images $J_1, J_2, \ldots, J_K$, to determine which 2D positions correspond to the same seed (and marker). Coordinate reconstructer 154 then reconstructs the 3D FL coordinates $R_1, R_2, \ldots, R_N$ of the seeds and the 3D FL coordinates $P_1, P_2, \ldots, P_M$ according to Step of the invention. In one embodiment of the invention, coordinate generator 154 stores each set of coordinates $R_i$ and $P_i$ for later recall and processing. By way of example only, the memory in which the 3D FL coordinates are stored may be memory typically associated with the personal computer of system 100 such as memory areas 135 or 140 (FIG. 3).

Coordinate correlator 156 maps each 3D FL marker point $P_i$ provided by coordinate generator 154 to its corresponding 3D US location $Q_i$ provided by data analyzer 152 according to Step 11 of the present invention. It then maps each 3D FL seed point $R_i$ to its corresponding 3D US location $S_i$. Improved image generator 158 then generates a 3D image that displays each seed's position within the 3D US image according to Step 13 of the invention. Then, according to step 13 of the present invention, a user may visualize the improved image on monitor 115.

FIG. 6 illustrates a screen shot 600 of a PC display according to one embodiment of GUI 150. FIG. 6 is given by way of example only. As can be seen in FIG. 6, GUI 150 has several unique features. The "Back" button 610 allows the user to backup to fix errors (e.g. move backward from Step 4 to Step 3). The "ArchiveSave" button 620 allows the user to save his work at any given step and to later resume the method at that step. As noted above, one of ordinary skill in the art will recognize that Steps 1–13 may be ordered differently than shown in FIG. 4 and yet be within the scope of this invention. GUI 150 allows the user of the inventive system to practice the steps of the inventive method in a manner flexible to the user.

As illustrated in FIG. 6, GUI 150 allows the user to select a 3D US image 630 from among a plurality of 3D US images 640. Likewise, GUI 150 allows the user to select FL images 650 for analysis. GUI 150 also allows the user to visualize the determined 3D seed positions with respect to the 3D US image.

While the above description is set forth in specific detail, these details should not be construed as limitations on the scope of the invention but rather as an exemplification of embodiments thereof. Other variations may occur to a skilled artisan while remaining within the spirit and scope of the invention. By way of example only, the invention may be used to identify objects in tissue other than the prostate. The inventive system and method may also be used for other medical therapies or other 3D medical imaging purposes. Still other non-medical 3D imaging uses of the invention will be apparent to those of ordinary skill in the art.

I claim:

1. A system for determining a position of at least one implanted object in a body, comprising:

an ultrasound imager configured to forming an ultrasound image of a portion of the body containing the at least one implanted object;

a fluoroscopy imager configured to form a plurality of fluoroscopic images of the portion of the body; and a computer system coupled to said ultrasound imager and to said fluoroscopy imager, said computer system processing the ultrasound image and the plurality of fluoroscopic images to calculate the position of the at least one implanted object in the body.

2. The system of claim 1, wherein said computer system includes:

a processor for processing the ultrasound image and the plurality of fluoroscopic images; and a monitor coupled to said processor and configured to display a three-dimensional image of the portion of the body showing the position of the at least one implanted object in the body.

3. The system of claim 2, wherein said computer system further includes a graphical user interface coupled to said processor, said graphical user interface enabling a user to interact with said processor.

4. The system of claim 3, wherein said graphical user interface includes:

a first data input adapted to receive data regarding the ultrasound image;

a second data input adapted to receive data regarding the plurality of fluoroscopic images; and a data analyzer coupled to said first data input and to said second data input and adapted to calculate from the ultrasound image a series of three-dimensional coordinates $Q_1, Q_2, \ldots, Q_M$ associated with M markers placed in the portion of the body and visible in the ultrasound image and the plurality of fluoroscopic images, wherein $M \geq 4$.

5. The system of claim 4, wherein said data analyzer is further adapted to calculate:

at least one set of two-dimensional coordinates for the at least one implanted object in each of the plurality of fluoroscopic images; and M sets of two-dimensional coordinates for the M markers in each of the plurality of fluoroscopic images.

6. The system of claim 5, wherein said graphical user interface further includes a coordinate reconstructor coupled to said data analyzer and adapted to determine:
 a series of three-dimensional coordinates $R_1, R_2, \ldots, R_N$ associated with N implanted objects; and
 a series of three-dimensional coordinates $P_1, P_2, \ldots, P_M$ associated with the M markers.

7. The system of claim 6, wherein said graphical user interface further includes a coordinate correlator adapted to associate each of the series of three-dimensional coordinates $P_i$ with each of the series of three-dimensional coordinates $Q_i$ for each of the M makers, wherein $1 \leq i \leq M$.

8. The system of claim 7, wherein said coordinate correlator is further adapted to determine a 3×3 matrix T and a 3×1 vector t by solving an optimization problem.

9. The system of claim 8, wherein:
 an initial estimate for (T,t) is found by solving a first optimization problem $$\min_{T,t} \sum_{i=1}^{M} \|Q_i - TP_i - t\|^2;$$

a subsequent estimate for (T,t) is found by solving a second optimization problem $$\max_{T,t} \sum_{j=1}^{N} I(TR_j + t),$$

wherein I(X) is a scalar intensity of point X in the ultrasound image; and
 if the second optimization problem has no unique solution, the subsequent estimate for (T,t) is found through a locally optimal solution.

10. The system of claim 8, wherein said coordinate correlator is further adapted to map each of the series of three-dimensional coordinates $R_1, R_2, \ldots, R_N$ to a series of three-dimensional coordinates $S_1, S_2, \ldots, S_N$ by a transformation $S_j = TR_j + t$, wherein $1 \leq j \leq N$.

11. The system of claim 1, wherein the at least one implanted object includes a plurality of brachytherapy seeds used in a radiation treatment of affected tissue.

12. A system for determining the three dimensional position of implanted objects, comprising:
 a computer system adapted to receive a three dimensional ultrasound image of a region containing the implanted objects and a plurality of two dimensional fluoroscopic images of the region, said computer system being adapted to form from said three dimensional ultrasound image and said plurality of two dimensional fluoroscopic images an improved three dimensional image of the region, said improved three dimensional image capable of indicating the location of each of the implanted objects; and
 a graphical user interface for determining the three dimensional position of the implanted objects with respect to the region, wherein said graphical user interface prompts and coordinates execution of a sequence of steps performed cooperatively by a user and said computer system and further comprises:
  a data input adapted to receive a number M corresponding to a number of implanted markers and a number N corresponding to a number of the implanted objects; and
  a data analyzer adapted to:
   locate the M highly visible implanted markers within the three dimensional ultrasound image, where $M \geq 4$; and
   store on a computer-readable medium a series $Q_1, Q_2, \ldots, Q_M$ for $1 \leq i \leq M$ wherein $Q_i$ corresponds to a unique set of three dimensional coordinates associated with each of the M highly visible markers.

13. The system of claim 12 wherein said data analyzer is further adapted to:
 locate each implanted seed and marker appearing in each image of said plurality of two dimensional fluoroscopic images; and
 store on a computer-readable medium a unique set of two dimensional coordinates corresponding to the location of each implanted seed and marker appearing in each of said two dimensional fluoroscopic images.

14. The system of claim 6 wherein said graphical user interface further comprises:
 a coordinate reconstructor adapted to determine a series $R_1, R_2, \ldots, R_N$ and $P_1, P_2, \ldots, P_M$ where $R_i$ and $P_i$ correspond to a unique set of derived three dimensional coordinates associated with each implanted seed and marker, respectively, appearing in said plurality of two dimensional fluoroscopic images.

15. The system of claim 13 wherein said graphical user interface further comprises:
 a coordinate correlator adapted to associate each said unique set of three dimensional FL coordinates $P_1$ for $1 \leq i \leq M$ corresponding to the location of each of the M highly visible markers with each said unique set of identified three dimensional US coordinates $Q_i$ for $1 \leq i \leq M$ corresponding to the same marker.

16. The system of claim 15 wherein said coordinate correlator is further adapted to:
 map each said unique set of derived three dimensional FL coordinates $R_i$ corresponding to an implanted seed to the three dimensional US coordinates $S_i$ corresponding to the same implanted seed by the transformation $S_i = TR_i + t$.

17. The system of claim 16 wherein said coordinate correlator is further adapted to determine a solution to an optimization problem.

18. The system of claim 16 wherein said coordinate correlator is further adapted to:
 determine a solution 3×3 matrix T and a 3×1 vector t wherein:
  an initial estimate for (T,t) is found by determining the unique solution to the optimization problem $$\min_{T,t} \sum_{i=1}^{M} \|Q_i - TP_i - t\|^2;$$

a final estimate is found by solving the optimization problem $$\max_{T,t} \sum_{i=1}^{N} I(TR_i + t);$$

and if the maximization problem has no unique solution, a locally optimal solution is determined.

19. A method for locating a plurality of implanted seeds, comprising the steps of:
 obtaining a three-dimensional ultrasound image of a region containing the plurality of implanted seeds;

obtaining a plurality of two-dimensional fluoroscopic images of the region;

matching the plurality of implanted seeds in the three-dimensional ultrasound image with corresponding ones in the plurality of two-dimensional fluoroscopic images; and calculating a plurality of three-dimensional coordinates of the plurality of implanted seeds by analyzing the three-dimensional ultrasound image and the plurality of two-dimensional fluoroscopic images.

20. The method of claim 19, further comprising the step of implanting a plurality of brachytherapy seeds used in a radiotherapy as the plurality of implanted seeds.

21. The method of claim 19, further comprising the step of placing M markers in the region, the M markers being visible in the three-dimensional ultrasound image and in the plurality of two-dimensional fluoroscopic images.

22. The method of claim 21, further comprising the steps of:

locating the M markers within the three-dimensional ultrasound image, wherein $M \geq 4$; and calculating a series of three-dimensional coordinates $Q_1$, $Q_2, \ldots, Q_M$ of the M markers by analyzing the three-dimensional ultrasound image.

23. The method of claim 22, further comprising the steps of:

locating the plurality of implanted seeds and the M markers in each of the plurality of two-dimensional fluoroscopic images;

calculating a first plural sets of two-dimensional coordinates for the plurality of implanted seeds appearing in the plurality of two-dimensional fluoroscopic images;

calculating a second plural sets of two-dimensional coordinates for the M markers appearing in the plurality of two-dimensional fluoroscopic images;

determining a first series of three-dimensional coordinates $R_1, R_2, \ldots, R_N$ of the plurality of implanted seeds from the first plural sets of two-dimensional coordinates, wherein N is a number of the plurality of implanted seeds; and determining a second series of three-dimensional coordinates $P_1, P_2, \ldots, P_M$ of the M markers from the second plural sets of two-dimensional coordinates.

24. The method of claim 23, further comprising the step of associating each $P_i$ with a corresponding $Q_i$, wherein $1 \leq i \leq M$.

25. The method of claim 24, further comprising the step of finding a series of three-dimensional coordinates $S_1, S_2, \ldots, S_N$ of the N implanted seeds by a transformation $S_j = TR_j + t$, wherein $1 \leq j \leq N$.

26. The method of claim 25, wherein the step of associating includes finding a 3×3 matrix T and a 3×1 vector t by determining a solution to an optimization problem.

27. A method for determining the three dimensional position of implanted seeds, comprising the steps of:

inputting a number M corresponding to a number of implanted markers and a number N corresponding to a number of implanted seeds;

obtaining a three dimensional ultrasound image of a region of implanted seeds;

obtaining a plurality of two dimensional fluoroscopic images of the region of implanted seeds;

forming an improved three dimensional image of the region of implanted seeds by analyzing data from said three dimensional ultrasound image in combination with data from said plurality of two dimensional fluoroscopic images; and identifying the location of each implanted seed in the region by analysis of said improved three dimensional image.

28. A method for determining the three dimensional position of implanted seeds, comprising the steps of:

obtaining a three dimensional ultrasound image of a region of implanted seeds;

obtaining a plurality of two dimensional fluoroscopic images of the region of implanted seeds;

locating M highly visible implanted markers within the three dimensional ultrasound image, where $M \geq 4$;

storing on a computer-readable medium a series $Q_1, Q_2, \ldots, Q_M$ for $1 \leq i \leq M$ wherein $Q_i$ corresponds to a unique set of three dimensional coordinates associated with each of the M highly visible markers;

forming an improved three dimensional image of the region of implanted seeds by analyzing data from said three dimensional ultrasound image in combination with data from said plurality of two dimensional fluoroscopic images; and identifying the location of each implanted seed in the region by analysis of said improved three dimensional image.

29. A method for determining the three dimensional position of implanted seeds, comprising the steps of:

obtaining a three dimensional ultrasound image of a region of implanted seeds;

obtaining a plurality of two dimensional fluoroscopic images of the region of implanted seeds;

locating each implanted seed and marker appearing in each image of said plurality of two dimensional fluoroscopic images;

storing on a computer-readable medium a unique set of two dimensional coordinates corresponding to the location of each implanted seed and marker appearing in each said two dimensional fluoroscopic image;

forming an improved three dimensional image of the region of implanted seeds by analyzing data from said three dimensional ultrasound image in combination with data from said plurality of two dimensional fluoroscopic images;

identifying the location of each implanted seed in the region by analysis of said improved three dimensional image; and determining series $R_1, R_2, \ldots, R$ and $P_1, P_2, \ldots, P_M$ where $R_i$ and $P_i$ correspond to a unique set of derived three dimensional FL coordinates associated with each implanted seed and marker, respectively, appearing in said plurality of two dimensional fluoroscopic images.

30. The method of claim 29 further comprising the step of:

associating each said unique set of three dimensional FL coordinates $P_i$ for $1 \leq i \leq M$ corresponding to the location of each of the M highly visible markers with each said unique set of identified three dimensional US coordinates $Q_i$ for $1 \leq i \leq M$ corresponding to the same implanted marker.

31. A method for determining the three dimensional position of implanted seeds, comprising the steps of:

obtaining a three dimensional ultrasound image of a region of implanted seeds;

obtaining a plurality of two dimensional fluoroscopic images of the region of implanted seeds;

forming an improved three dimensional image of the region of implanted seeds by analyzing data from said three dimensional ultrasound image in combination with data from said plurality of two dimensional fluoroscopic images, wherein said step of forming an improved three dimensional image further comprises mapping each said unique set of derived three dimensional FL coordinates $R_i$, corresponding to an implanted seed to its 3D US location $S_i$; and identifying the location of each implanted seed in the region by analysis of said improved three dimensional image.

32. The method of claim 31 wherein said act of associating further comprises determining a solution to an optimization problem.

33. The method of claim 32 wherein said step of determining a solution to an optimization problem further comprises:

determining a solution 3×3 matrix T and a 3×1 vector t wherein:
an initial estimate for (T,t) is found by determining the unique solution to the optimization problem $$\min_{T,t} \sum_{i=1}^{M} \|Q_i - TP_i - t\|^2;$$

a final estimate is found by solving the optimization problem $$\max_{T,t} \sum_{i=1}^{N} I(TR_i + t);$$

if the maximization problem has no unique solution, a locally optimal solution is determined.

34. A computer-generated graphical user interface for determining positions of a plurality of brachytherapy seeds with respect to an implanted region, the graphical user interface prompting and coordinating execution of a sequence of steps performed cooperatively by a user and a computer processor, said sequence of steps comprising:

obtaining a three-dimensional ultrasound image of the implanted region;

obtaining a plurality of two-dimensional fluoroscopic images of the implanted region;

forming an improved three-dimensional image of the implanted region by analyzing the three-dimensional ultrasound image in combination with the plurality of two-dimensional fluoroscopic images; and identifying a position for each of the plurality of brachytherapy seeds in the implanted region in the improved three-dimensional image.

35. The graphical user interface of claim 34, wherein the plurality of brachytherapy seeds are used in radiotherapy treatment of an abnormal tissue in the implanted region.

36. The graphical user interface of claim 34, wherein said sequence of steps further comprises inputting a number M corresponding to a number of markers and a number N corresponding to a number of the plurality of brachytherapy seeds in the implanted region.

37. The graphical user interface of claim 36, wherein said sequence of steps further comprises:

locating the M markers within the three-dimensional ultrasound image, where $M \geq 4$; and storing on a computer-readable medium a series $Q_1$, $Q_2$, ..., $Q_M$ of three-dimensional coordinates associated with the M markers.

38. The graphical user interface of claim 37, wherein said sequence of steps further comprises:

locating the N brachytherapy seeds and the M markers appearing in each of said plurality of two-dimensional fluoroscopic images;

storing on the computer-readable medium a plural sets of two-dimensional coordinates for the N brachytherapy seeds and the M markers appearing in each of said plurality of two-dimensional fluoroscopic images; and deriving a first series $R_1, R_2, \ldots, R_N$ of three-dimensional coordinates for the N brachytherapy seeds and a second series $P_1, P_2, \ldots, P_M$ of three-dimensional coordinates for the M markers from the plural sets of two-dimensional coordinates.

39. The graphical user interface of claim 38, wherein said sequence of steps further comprises associating each $P_i$ with a corresponding $Q_i$ for $1 \leq i \leq M$.

40. The graphical user interface of claim 39, wherein said step of associating further comprises determining a solution to an optimization problem.

41. The graphical user interface of claim 38, wherein said sequence of steps further comprises finding a matrix T and a 3×1 vector t through an optimization process, wherein:

an initial estimate for (T,t) is found by solving a minimization problem $$\min_{T,t} \sum_{i=1}^{M} \|Q_i - TP_i - t\|^2;$$

a second estimate for (T,t) is found by solving a maximization $$\max_{T,t} \sum_{j=1}^{N} I(TR_j + t),$$

wherein I(X) is a scalar intensity of point X in the three-dimensional ultrasound image; and if the maximization problem has no unique solution, the second estimation for (T,t) is found through a locally optimal solution.

42. The graphical user interface of claim 41, wherein said sequence of steps further comprises calculating a series of derived three-dimensional coordinates $S_1, S_2, \ldots, S_N$ of the N brachytherapy seeds, wherein $S_j = TR_j + t$ for $1 \leq j \leq N$.

43. A computer-generated graphical user interface for determining the three dimensional position of brachytherapy seeds with respect to an implanted region wherein said graphical user interface prompts and coordinates execution of a sequence of steps performed cooperatively by a user and a computer processor, said sequence of steps comprising:

inputting a number M corresponding to a number of implanted markers and a number N corresponding to the number of implanted seeds;

obtaining a three dimensional ultrasound image of a region of implanted seeds;

obtaining a plurality of two dimensional fluoroscopic images of the region of implanted seeds;

forming an improved three dimensional image of the region of implanted seeds by analyzing data from said three dimensional ultrasound image in combination with data from said plurality of two dimensional fluoroscopic images; and identifying the location of each implanted seed in the region by analysis of said improved three dimensional image.

44. A computer-generated graphical user interface for determining the three dimensional position of brachytherapy seeds with respect to an implanted region wherein said graphical user interface prompts and coordinates execution of a sequence of steps performed cooperatively by a user and a computer processor, said sequence of steps comprising:

obtaining a three dimensional ultrasound image of a region of implanted seeds;

obtaining a plurality of two dimensional fluoroscopic images of the region of implanted seeds;

locating M highly visible implanted markers within the three dimensional ultrasound image, where $M \geq 4$;

storing on a computer-readable medium a series $Q_1, Q_2, \ldots, Q_M$ for $1 \leq i \leq M$ wherein $Q_i$ corresponds to a unique set of three dimensional coordinates associated with each of the at least four highly visible markers;

forming an improved three dimensional image of the region of implanted seeds by analyzing data from said three dimensional ultrasound image in combination with data from said plurality of two dimensional fluoroscopic images; and identifying the location of each implanted seed in the region by analysis of said improved three dimensional image.

45. A computer-generated graphical user interface for determining the three dimensional position of brachytherapy seeds with respect to an implanted region wherein said graphical user interface prompts and coordinates execution of a sequence of steps performed cooperatively by a user and a computer processor, said sequence of steps comprising:

obtaining a three dimensional ultrasound image of a region of implanted seeds;

obtaining a plurality of two dimensional fluoroscopic images of the region of implanted seeds;

locating each implanted seed and marker appearing in each image of said plurality of two dimensional fluoroscopic images;

storing on a computer-readable medium a unique set of two dimensional coordinates corresponding to the location of each implanted seed and marker appearing in each said two dimensional fluoroscopic image;

determining a series $R_1, R_2, \ldots, R_N$ and $P_1, P_2, \ldots, P_M$ where $R_i$ and $P_i$ correspond to a unique set of derived three dimensional coordinates associated with each implanted seed and marker, respectively, appearing in said plurality of two dimensional fluoroscopic images;

forming an improved three dimensional image of the region of implanted seeds by analyzing data from said three dimensional ultrasound image in combination with data from said plurality of two dimensional fluoroscopic images; and identifying the location of each implanted seed in the region by analysis of said improved three dimensional image.

46. The graphical user interface of claim 45 wherein said graphical user interface further prompts and coordinates the step of:

associating each said unique set of derived three dimensional FL coordinates P, for $1 \leq i \leq M$ corresponding to the location of each of the M highly visible markers with each said unique set of identified three dimensional coordinates $Q_i$ for $1 \leq i \leq M$ corresponding to the same marker.

47. The graphical user interface of claim 45 wherein said graphical user interface further prompts and coordinates the step of:

mapping each said unique set of derived three dimensional FL coordinates $R_i$ corresponding to an implanted seed to its 3D ultrasound coordinate $S_i$.

48. The graphical user interface of claim 47 wherein said step of associating further comprises determining a solution to an optimization problem.

49. The graphical user interface of claim 48 wherein said step of determining a solution to an optimization problem further comprises:

determining a solution $3 \times 3$ matrix T and a $3 \times 1$ vector t wherein:

an initial estimate for (T,t) is found by determining the unique solution to the optimization problem $$\min_{T,t} \sum_{i=1}^{M} \|Q_i - TP_i - t\|^2;$$

a final estimate is found by solving the optimization problem $$\max_{T,t} \sum_{i=1}^{N} I(TR_i + t);$$

and if the maximization problem has no unique solution, a locally optimal solution is determined.

50. A computer-readable medium on which is embodied a set of programmed instructions that causes a processor to perform a sequence of steps, said sequence of steps comprising:

obtaining a three-dimensional ultrasound image of a region containing a plurality of implanted seeds;

obtaining a plurality of two-dimensional fluoroscopic images of the region;

forming an improved three-dimensional image of the region by analyzing the three-dimensional ultrasound image in combination with the plurality of two-dimensional fluoroscopic images; and identifying a location for each of the plurality of implanted seeds in the region by analysis of the improved three-dimensional image.

51. A process for locating a plurality of objects in a region, comprising the steps of:

placing a plurality of markers in the region, the plurality of markers being visible via a first imaging mode and a second imaging mode and being distinguishable from the plurality of objects;

forming a first image of the first imaging mode of the region;

identifying a first plurality of markings in the first image corresponding to the plurality of markers;

forming a second image and a third image of the second imaging mode of the region;

identifying a second plurality of markings in the second image corresponding to the plurality of markers;

identifying a third plurality of markings in the third image corresponding to the plurality of markers;

establishing a correlation between the first image, the second image, and the third image by matching the first plurality of markings with the second plurality of markings and the third plurality of markings;

deriving a set of object coordinates corresponding to the plurality of objects in the second image and in the third image; and calculating a series of three-dimensional coordinates for the plurality of objects in response to the correlation between the first image, the second image, and the third image and to the set of object coordinates.

52. The process of claim 51, further comprising the step of implanting a plurality of brachytherapy seeds used in a radiation therapy into a portion of a patient's body as the plurality of objects in the region.

53. The process of claim 51, wherein said step of placing a plurality of markers in the region includes placing at least four markers uncoplanar with each other in the region.

54. The process of claim 51, wherein:

said step of forming a first image of the first imaging mode includes forming a three-dimensional ultrasound image of the region; and said step of forming a second image and a third image of the second imaging mode includes forming a plurality of two-dimensional fluoroscopic images of the region.

55. The process of claim 51, wherein:

said step of identifying a first plurality of markings includes deriving a first set of marker coordinates $Q_1, Q_2, \ldots, Q_M$ for the plurality of markers, wherein $M \geq 4$ is a number of the markers;

said steps of identifying a second plurality of markings identifying a third plurality of markings include deriving a second set of marker coordinates $P_1, P_2, \ldots, P_M$ for the M markers; and said step of deriving a set of coordinates corresponding to the plurality of objects in the second image and in the third image includes deriving a set of object coordinates $R_1, R_2, \ldots, R_N$, wherein N is a number of the plurality of objects.

56. The process of claim 55, wherein said step establishing a correlation between the first image, the second image, and the third image includes a step of finding a 3×3 matrix T and a 3×1 vector t by solving a first optimization problem $$\min_{T,t} \sum_{i=1}^{M} \|Q_i - TP_i - t\|^2.$$

57. The process of claim 56, wherein said step of finding a 3×3 matrix T and a 3×1 vector t further includes solving a second optimization problem $$\max_{T,t} \sum_{j=1}^{N} I(TR_j + t),$$

wherein I(X) is a scalar intensity at a point X in the first image.

58. The process of claim 57, wherein said step of finding a 3×3 matrix T and a 3×1 vector t further includes solving a localized optimization problem in response to the second optimization problem not having a unique solution.

59. The process of claim 56, wherein said step of calculating a series of three-dimensional coordinates for the plurality of objects includes deriving the series of three-dimensional coordinates $S_1, S_2, \ldots, S_N$ of the N implanted seeds by a transformation $S_j = TR_j + t$, wherein $1 \leq j \leq N$.

60. The process of claim 51, generating a three-dimensional visual display of the region indicating the plurality of objects in accordance with the series of three-dimensional coordinates for the plurality of objects.

* * * * *

UNITED STATES PATENT AND TRADEMARK OFFICE
CERTIFICATE OF CORRECTION

PATENT NO.   : 6,549,802 B2
DATED        : April 15, 2003
INVENTOR(S)  : Kenneth B. Thornton It is certified that error appears in the above-identified patent and that said Letters Patent is hereby corrected as shown below:

Column 12,
Line 6, please replace "$1 \geq i \geq M$" with -- $1 \leq i \leq M$ --.

Column 14,
Line 16, please replace "$1 \geq i \geq M$" with -- $1 \leq i \leq M$ --.
Line 50, please replace "$R_1, R_2, ..., R$" with -- $R_1, R_2, ..., R_N$ --.

Column 16,
Line 21, immediately following "comprises finding a", please insert -- 3 x 3 --.

Column 17,
Line 31, please indent the margin before "obtaining".

Column 18,
Line 35, please correct the margin before "obtaining".

Column 20,
Lines 2, 9 and 21, please replace "Tand" with -- T and --.

Signed and Sealed this

Sixteenth Day of December, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,549,802 B2
DATED : April 15, 2003
INVENTOR(S) : Kenneth B. Thornton It is certified that error appears in the above-identified patent and that said Letters Patent is hereby corrected as shown below:

Column 12,
Line 6, please replace "$1 \geq i \geq M$" with -- $1 \leq i \leq M$ --.

Column 14,
Line 16, please replace "$1 \geq i \geq M$" with -- $1 \leq i \leq M$ --.
Line 50, please replace "$R_1, R_2, ..., R$" with -- $R_1, R_2, ..., R_N$ --.

Column 16,
Line 21, immediately following "comprises finding a", please insert -- 3 x 3 --.

Column 17,
Line 31, please indent the margin before "obtaining".

Column 18,
Line 35, please correct the margin before "obtaining".

Column 20,
Lines 2, 9 and 21, please replace "Tand" with -- T and --.

Signed and Sealed this

Thirteenth Day of July, 2004

JON W. DUDAS
*Acting Director of the United States Patent and Trademark Office*